(12) United States Patent
Kertzner et al.

(10) Patent No.: US 8,114,090 B2
(45) Date of Patent: Feb. 14, 2012

(54) DRILL CENTERING TOOL FOR REMOVAL OF ORTHOPEDIC PLUG

(76) Inventors: Richard I. Kertzner, Calabasas, CA (US); Michael Wang, Arcadia, CA (US)

( * ) Notice: Subject to any disclaimer, the term of this patent is extended or adjusted under 35 U.S.C. 154(b) by 1361 days.

(21) Appl. No.: 11/031,840

(22) Filed: Jan. 6, 2005

(65) Prior Publication Data

US 2006/0149269 A1   Jul. 6, 2006

(51) Int. Cl.
*A61B 17/58* (2006.01)
*A61B 17/00* (2006.01)

(52) U.S. Cl. ............... 606/96; 606/87; 606/80
(58) Field of Classification Search ............ 606/80, 606/95, 96, 99, 86 R, 87
See application file for complete search history.

(56) References Cited

U.S. PATENT DOCUMENTS

| | | | | |
|---|---|---|---|---|
| 4,388,014 A | * | 6/1983 | Wlodkowski et al. | 403/369 |
| 4,523,587 A | * | 6/1985 | Frey | 606/86 R |
| 4,682,821 A | * | 7/1987 | Strazis | 301/37.42 |
| 5,628,591 A | * | 5/1997 | Gamble | 408/75 |
| 5,916,151 A | * | 6/1999 | Charters | 600/224 |
| 6,579,321 B1 | * | 6/2003 | Gordon et al. | 623/17.16 |
| 2003/0014068 A1 | * | 1/2003 | Bonutti et al. | 606/190 |
| 2004/0092940 A1 | * | 5/2004 | Zwirnmann | 606/80 |

* cited by examiner

*Primary Examiner* — Thomas C. Barrett
*Assistant Examiner* — Michael T Schaper
(74) *Attorney, Agent, or Firm* — Elliott N. Kramsky

(57) ABSTRACT

A tool centers an elongated drill bit within an elongated canal surrounded by bone tissue. A sleeve having an expandable diameter is internally threaded. The sleeve threadedly engages an externally-threaded cylindrical guide. A key includes a handle at one end of an elongated rod. The rod includes transversely-protruding buttons for engaging the guide so that rotation of the handle produces rotation of the guide to cause radial expansion of the sleeve. This results in symmetrical contacting of the interior surfaces of the bone tissue, thereby creating a vertical, centered channel with respect to the bone, that extends through the tool for guiding the drill bit.

15 Claims, 5 Drawing Sheets

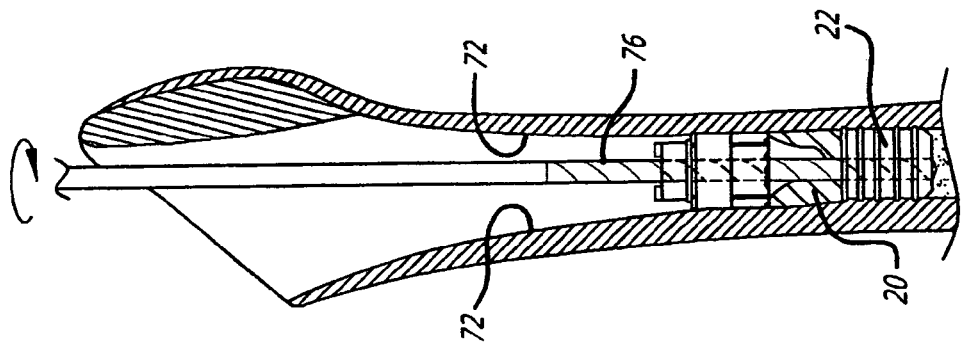
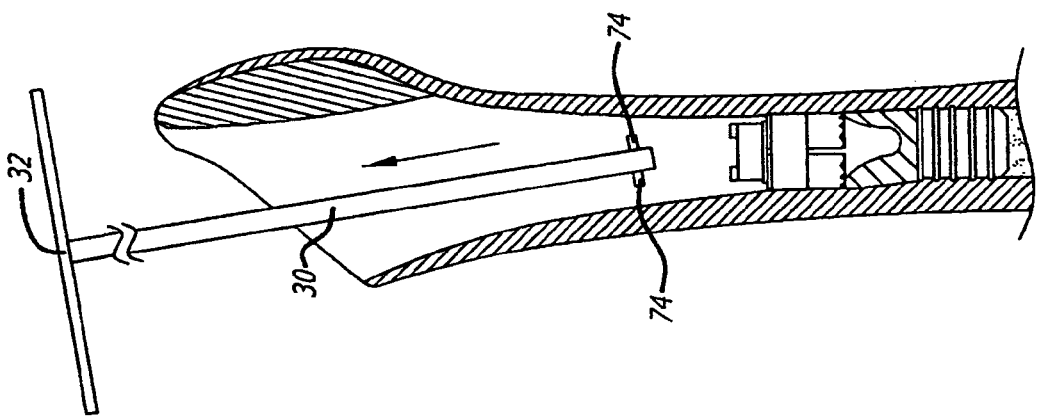
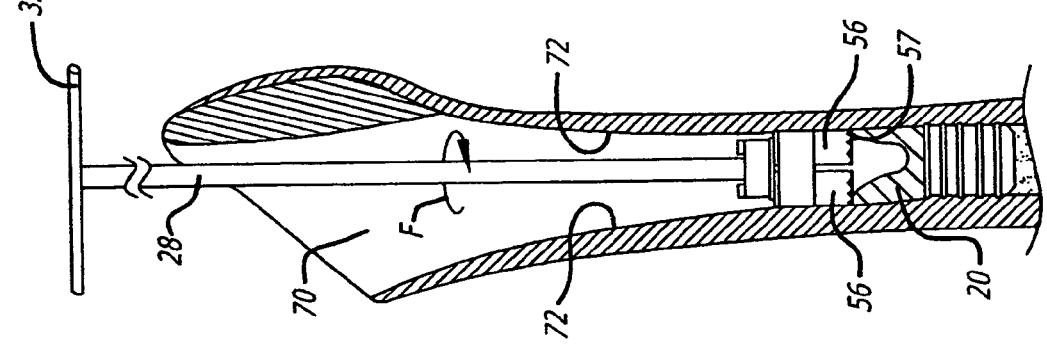
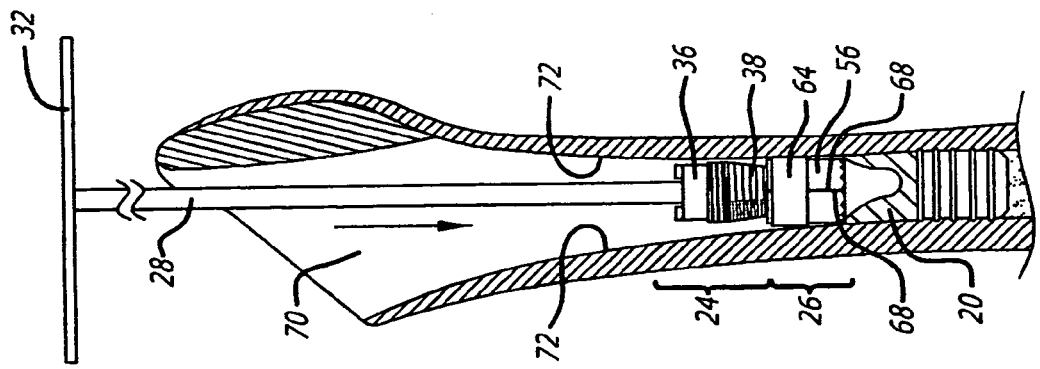

DRILL CENTERING TOOL FOR REMOVAL OF ORTHOPEDIC PLUG

BACKGROUND

1. Field of the Invention

The present invention relates to tools for facilitating orthopedic procedures. More particularly, this invention pertains to a tool for reliably centering a drill bit within the femoral canal for facilitating removal of the plug of cementous material that remains after removal of a worn hip prosthesis.

2. Description of the Prior Art

While primary total hip arthroplasty (THA) generally produces a successful and long-lasting result, annually about one percent of existing hip replacements require revision. FIG. 1 is a side elevation view in partial cross-section of the region of a hip replacement showing a prosthesis 10 fixed within a human femur 12. The prosthesis may be fabricated of, for example, stainless steel and includes a metal ball or prosthetic head 14 that is, in turn, coupled to a prosthetic hip socket (not shown). The lower portion of the prosthesis 10 extends to and terminates in a elongated stem 16. The stem 16 extends into the femoral canal.

The stem 16 is anchored to the surrounding bone of the femoral canal by means of cement 18. The hardened cement 18 (a mixture of a monomer and a polymer) surrounds the stem 16 and extends beneath, forming a solid region known as a cement "plug". A stop or restrictor 22 of plastic may have been inserted within the femoral canal during the procedure to increase backpressure (and thereby improving the quality of the cement-to-bone tissue bond) on the cement during hardening.

A gradual breakdown or loosening of the bond between the cement that holds the prosthesis within the patient's femur and the surrounding bone generally occurs over time, limiting the useful life of the existing procedure to about 10 to 20 years. Such loosening of the bond leads to the patient's experiencing pain. When such pain becomes significant, revision is required. This involves removal of the existing prosthesis and attachment of a new prosthesis in its place. The required surgical procedure involves removal of existing cement and the optional restrictor, in addition to the existing prosthesis, prior to insertion of a new device. The subsequent hip replacement often employs a non-cement fixation technique due to the thinning and reduced adhesion of existing bone tissue. The latter prosthesis may, for example, be formed with beaded or mesh-like surfaces that encourage interdigitation of bone tissue thereon. An alternative technique is to inject pressurized cement into a femoral canal that has been cleared of all debris. Generally, revision hip replacement can achieve a long lasting result and provide substantial pain relief.

The revision surgery is begun by removal of all foreign objects from the femoral canal. The existing prosthesis is readily removed, leaving the mantle of hardened cement and, possibly, the plastic restrictor in the canal. Removal of the structures associated with the existing prosthesis becomes more complicated and risky as one progresses further and further from the top or head of the bone into the femoral canal. While the uppermost cement is not as difficult to remove, visibility and accessibility limitations crop up as the surgeon proceeds further. Maintenance of adequate lighting is difficult and further obscuration is caused by the increased presence of blood once the upper regions of the cement have been removed (by, for example, power burrs, hand-held chisels, ultrasound, etc.), leaving the cement plug (and, perhaps, the plastic restrictor).

Removal of the remaining plug (and optional restrictor) is commonly accomplished by a number of tools and techniques including elongated drill bits, burrs or hand-held chisels to break through, fragment or create a hole in the plug. An elongated tool having a hooked end can then be inserted through the obstruction and an upwardly-directed force applied to lift and remove it.

The process of making a hole through the cement plug with an elongated drill bit is complicated by an environment that is obscure, small, remote and adjacent bone tissue whose integrity must be protected. Visibility and alignment difficulties in the plug region create a very dangerous environment in which to operate a drill bit, burr or chisel. Misalignment may result in the perforation of bone tissue. X-ray or like equipment is often employed to assure proper centering of potentially-harmful tools within the femoral canal. Another method of obtaining visibility is the excising of a "window" in the bone. This complicates the surgery, increasing its duration, the loss of blood and the risk of subsequent bone fracture.

U.S. Pat. No. 5,649,930 of Kertzner et al. covering "Orthopedic Centering Tool" teaches a tool for guiding a surgical drill bit through a cement plug within the femoral canal. Such tool provides a means for centering a drill bit that is not dependent upon direct observation of the drill bit within the interior of the femoral canal during surgery. Rather, it enables the surgeon to be assured that the bit is properly directed through an alignment procedure that occurs before the drill bit enters the canal.

The patented tool includes an adjustable frame comprising a pair of right angle sections mounted in a mirror image relationship. The sections are adjustably clamped to one another and, in turn, secure a vertical sleeve for guiding a surgical drill bit and a horizontal sleeve for accommodating an anchor pin. Various clamps permit a surgeon to adjust the tool so that the drill bit is guided to the approximate center of the femoral canal immediately below the plug while the pin anchors the frame to the bone.

While providing a number of advantages over such procedures as x-rays and the cutting of a window into the bone, the above-described tool is somewhat awkward to adjust during an operation. Such adjustment is undertaken within a difficult environment that includes blood, cement and bone fragments. Time limitations also complicate use of the tool. They may be due, for example, to the patient's tolerance for anesthesia. These and related factors complicate the surgeon's ability to perform the multiple adjustments required to assure that the drill bit has been positioned properly with respect to the bone.

SUMMARY OF THE INVENTION

The present invention addresses the preceding and other shortcomings of the invention by providing a tool for centering a drill bit within an elongated canal at the interior of bone tissue. Such tool includes an exteriorly-threaded guide and a hollow, interiorly-threaded sleeve.

The sleeve is threadedly engaged to the guide, its diameter being responsive to rotation of the guide. A key is provided. Such key comprises an elongated rod having a handle fixed to an end. The elongated rod has a plurality of transversely-protruding tabs for engaging the guide so that rotation of the key produces rotation of the guide. In this way, the diameter of the sleeve is controlled by rotation of the handle.

The preceding and other features of the invention will become further apparent from the detailed description that follows. Such description is accompanied by a set of drawing figures. Numerals of the drawings, corresponding to those of the written description, point to the features of the invention with like numerals referring to like features throughout both the written description and the drawings.

BRIEF DESCRIPTION OF THE DRAWINGS

FIGS. 5A through 5D are a series of partial section side elevation views for illustrating the operation of the tool of the invention.

DETAILED DESCRIPTION OF THE PREFERRED EMBODIMENT

Figure 2A:
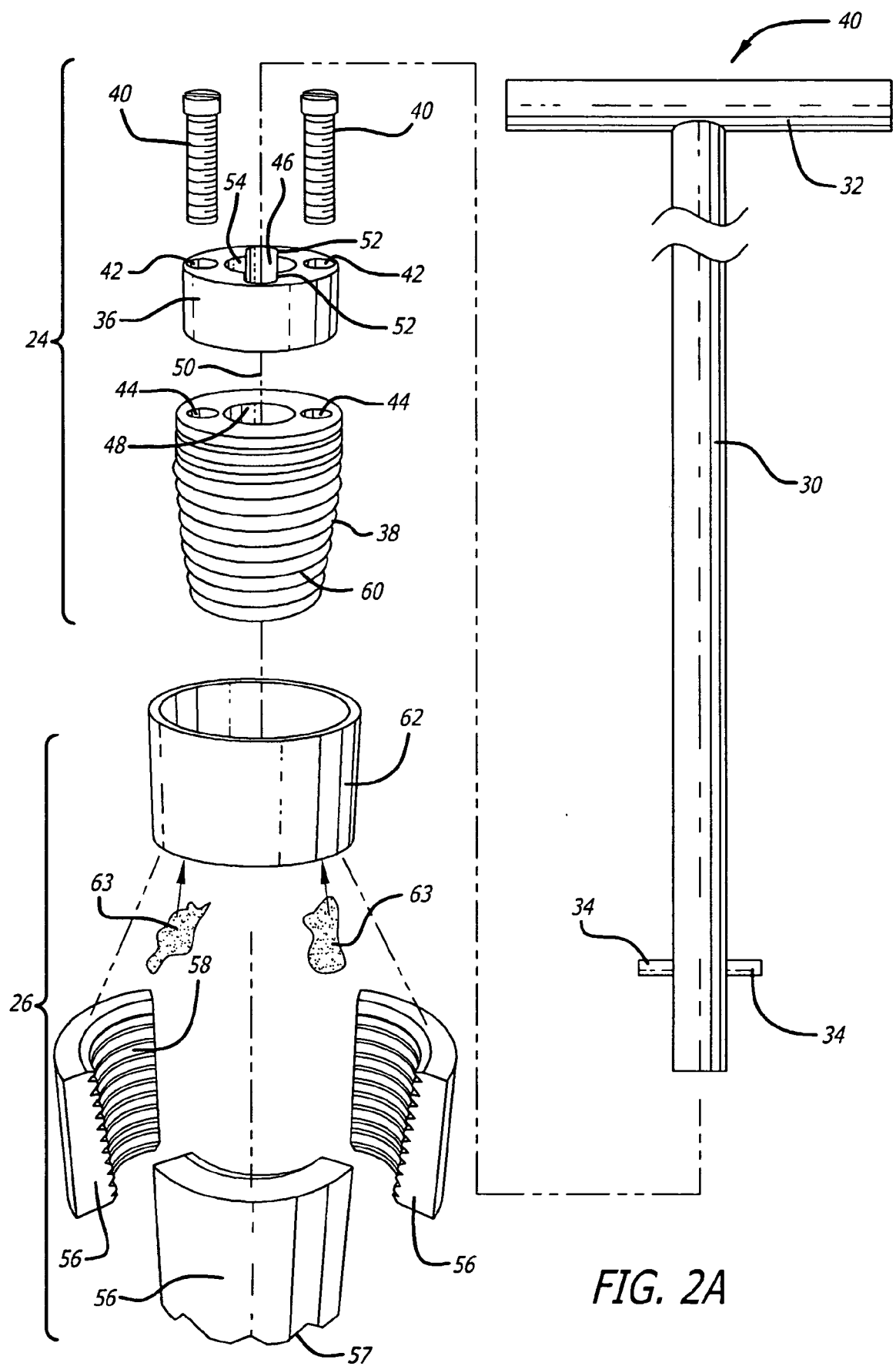
FIGS. 2A and 2B are exploded and fragmentary assembled perspective views of the tool and the guide and sleeve of the invention respectively.
Figure 2B:
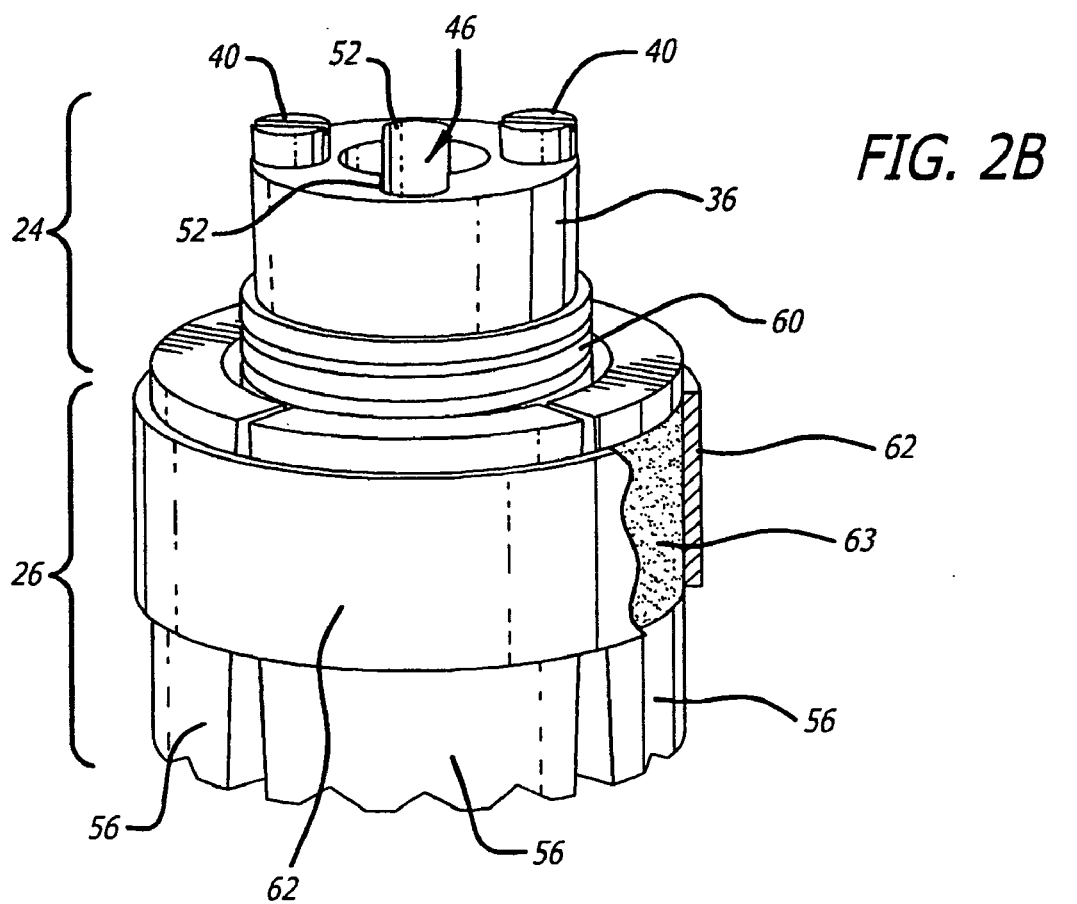

FIGS. 2A and 2B are exploded and fragmentary assembled perspective views of the tool of the invention. Viewed in combination, the tool generally comprises an exteriorly-threaded guide 24, an interiorly-threaded sleeve 26, and a key 28 that consists of an elongated rod 30 and a handle 32. A pair of tabs 34 extend transversely from the surface of the elongated rod 30. The tabs 34 may comprise, for example, a single pin whose length exceeds the thickness or diameter of the rod 30.

The guide 24 comprises an annular collar 36 and an exteriorly-threaded body 38. A pair of screws 40 secures the collar 36 to the body 38 by engaging aligned pairs of internally-threaded apertures 42, 44 respectively.

Once secured to one another, the circular void center 46 of the collar 36 is mated with a central aperture 48 of the body 38. Such aperture 48 is aligned with the longitudinal axis of rotation 50 of the body 38. The center 46 of the collar 36 and the central aperture 48 of the body 38, in combination, provide a channel for receiving the key 28. Entry into such channel is provided by opposed indentations 52 in an upper portion 54 of the annular collar 36. Such indentations 52 are directed radially from the void center 46 of the collar 36 to permit passage of the tabs 34 that protrude outwardly from the elongated shaft 30 of the key 28.

The interiorly-threaded sleeve 26 comprises an expandable configuration of three sleeve segments 56. When mated, the sleeve segments 56 form a generally-cylindrical shape. Such shape may be radially expanded, by controllable expansion of the separation between individual sleeve segments 56. This occurs in response to rotation of the shaft 30 of the key 28 when inserted into the channel formed by the void center 46 of the collar 36 and the central aperture 48 of the body 38. The resultant expansion of the sleeve is described below.

The bottom edge 57 of each sleeve segment 56 (and of the sleeve 26) is serrated. As will be shown below, such serration of the edge 57 enables the sleeve to engage the cement and plug during operation. This permits the sleeve 26 to remain in place as the guide 24 is advanced downwardly with respect to the sleeve 26 by rotation of the key 28.

As can be seen, the interiorly-threaded surface 58 of a representative sleeve segment 56 is tapered to create, in combination, a larger diameter at the top than at the bottom of the expandable sleeve 26. As such, the internally threaded surface 58 of the sleeve 26 matches the exteriorly threaded surface 60 of the tapered guide body 38. This enables the threads at the exterior surface of the guide body 38 to mate with those at the interior of the expandable sleeve 26 through rotation of the guide body 38 (in response to rotation of the shaft 30 of the key 28).

An elastic band 62 surrounds and exerts an inwardly-directed retention force upon the segments 56 of the expandable sleeve 26. The band 62 is preferably of rubber or like elastic material. It may comprise, for example, commercially-available bicycle tubing manufactured by Trek Bicycle Corporation of Waterloo, Wis. and marketed under the trademark "BONTRAGER XXX LITE".

The elastic band 62 is secured to the outer surfaces to the segments by means of an adhesive 63. An appropriate commercially-available adhesive for securing the elastic band 62 to the segments 56 of the expandable sleeve 26 is the gel containing cyanoacrylate manufactured by Henkel Loctite Corporation of Rocky Hill, Conn. and marketed under the trademark "QUICKTITE SUPER GLUE".

Figure 3:
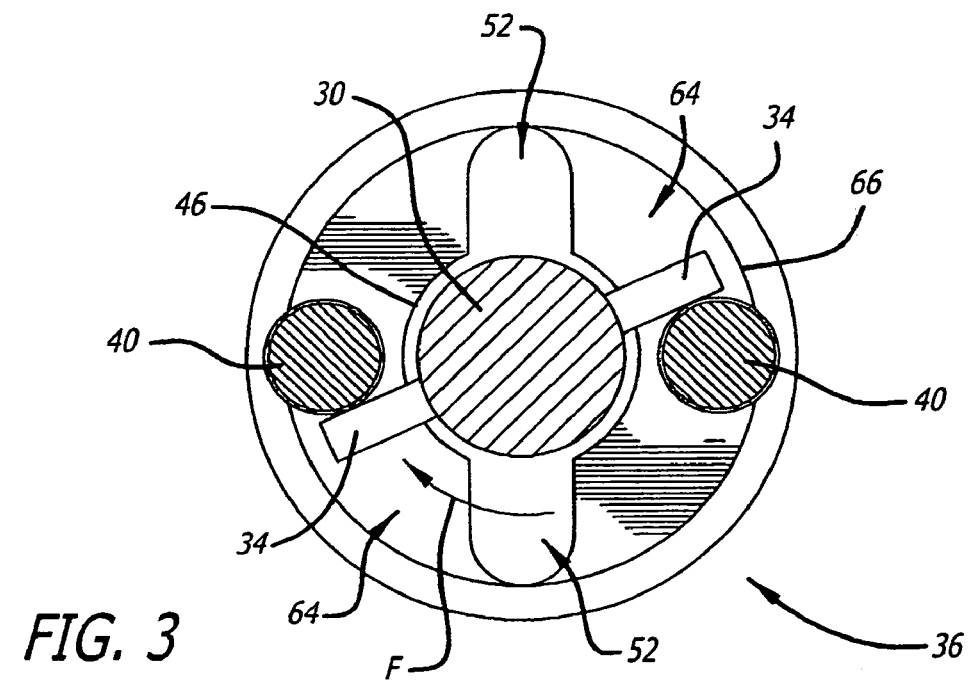
FIG. 3 is a bottom plan view of the collar for a guide of a tool in accordance with the invention.

As mentioned above, rotation of the guide body 38, which is fixed to the collar 36, occurs in response to rotation of the key 28. FIG. 3 is a bottom plan view of the collar 36 with the elongated shaft 30 inserted. As can be seen, the bottom of the collar 36, which is fixed to the body 38 of the guide 24 by means of the screws 40, includes an annular channel 64 that is defined and bounded by a peripheral ridge 66. The annular channel 64 is arranged to receive the tabs 34 of the elongated shaft 30 of the key 28 after insertion through the recesses 52 in the upper portion of the collar 36.

Rotation of the guide 24 in response to rotation of the key 28 occurs by the coordinated rotational forces F exerted by the tabs 34 upon contact with the screws 40 that extend through the annular channel 64.

Figure 4A:
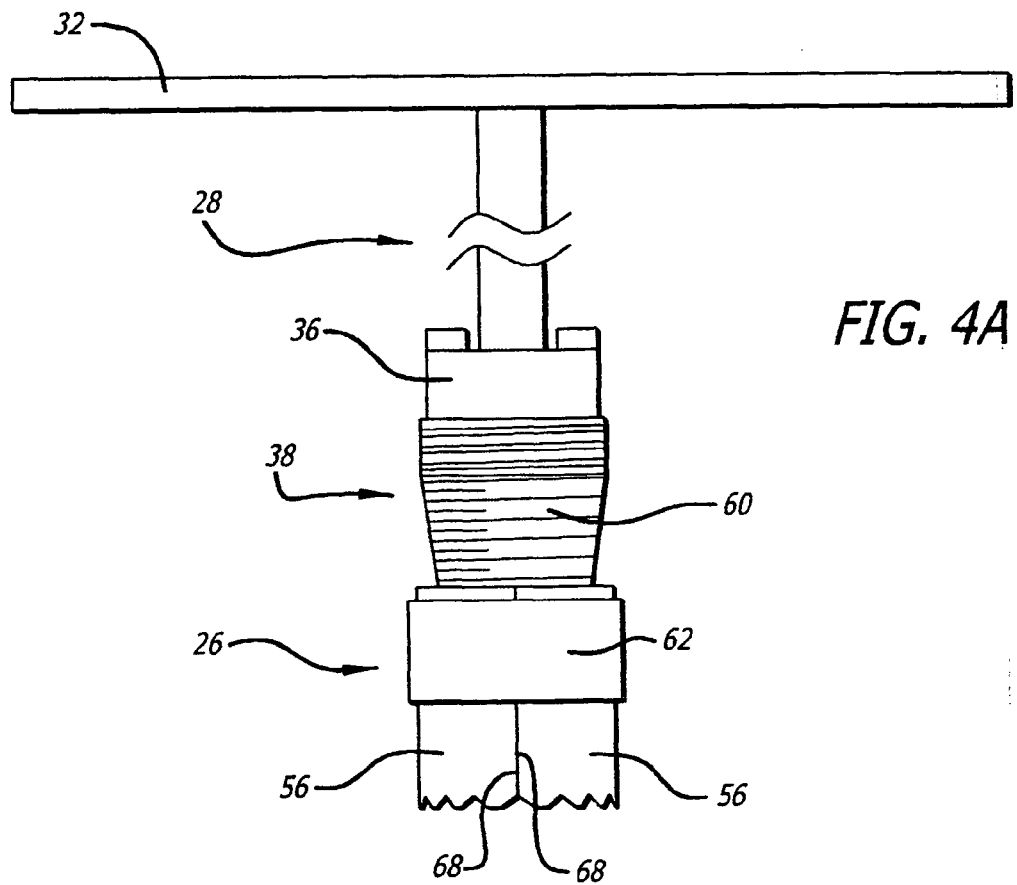
FIGS. 4A and 4B are a series of views for illustrating the expansion of the sleeve in response to rotation of the key of the invention.
Figure 4B:
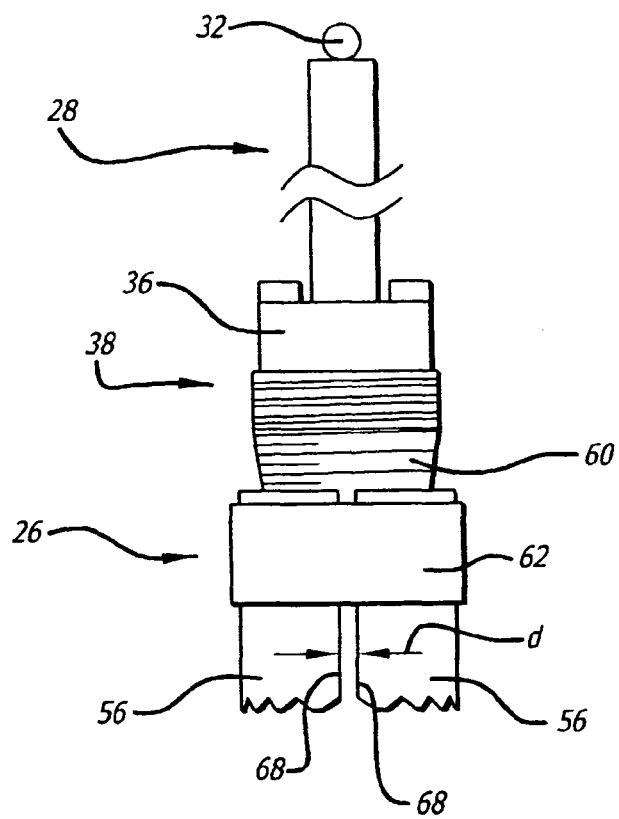

FIGS. 4A and 4B are a pair of views for illustrating the expansion of the sleeve 26 in response to rotation of the key 28. Such rotation is occasioned by twisting of the handle 32. FIG. 4B illustrates the tool after a quarter-turn of the handle 32 of the key 28. As can be seen, upon rotation of the key 28, the exteriorly-threaded body 38 of the guide, whose threaded exterior surface 60 is mated with the interiorly-threaded expandable sleeve 26, travels downwardly with respect to the sleeve 26. Due to the reciprocal tapered shapes of the outer surface of the body 38 and the interior surfaces of the sleeve segments 56, the intrusion of the body 38 into the interior of the sleeve 26 causes separation, by an amount d, to occur between longitudinal edges 68, 68 of adjacent sleeve segments 56. Such separation causes an expansion of the circumference of the expandable sleeve 26 by a total amount of approximately 3 d.

FIGS. 5A through 5D are a series of partial section side elevation views for illustrating the operation of the tool of the invention. The tool is prepared for centering an elongated drill bit within a femoral canal 70 after removal of a prosthesis. This is begun by inserting the key 28 into the collar 36 that is fixed atop the tapered body 38 of the guide 24. As illustrated in FIG. 5A, the assembled device, with the tapered body 38 seated at the top of the expandable sleeve 26, is ready to be inserted into the femoral canal 70. It is gently lowered into the canal 70 until downward movement is terminated by contact with the plug 20.

The sleeve members 56, held together at this time by the elastic member 64, are in substantial contact with each other along mating longitudinal edges 68. As a result, the expandable sleeve 26 is of relatively minimal diameter, providing clearance with the inner wall 72 of the bone in the region of the cement plug 20.

FIG. 5B illustrates the configuration of the tool 10 upon rotation of the handle 32 of the key 28. The serrated bottom edge 57 of the sleeve 26 create's a turning resistance force, occasioned by the application of downwardly-acting pressure upon the handle 32 and the weight of the tool, between the sleeve 26 and the cement plug 20. Such force prevents the rotation of the sleeve 26 with the guide 24 that would otherwise occur when the key 28 is rotated.

By allowing rotation of the guide 24 to occur relative to the sleeve 26, expansion of the diameter of the diameter and circumference of the sleeve 26 will occur within the canal 70 in accordance with the process described in conjunction with FIGS. 4A and 4B above. The surgeon continues to twist the handle 32, gradually expanding the diameter of the sleeve 26 until resistance to further twisting is felt. This indicates that the periphery of the sleeve 26 has expanded to contact the inner wall 72 of the bone.

Once sufficient contact with the inner wall 72 of the bone is sensed, twisting of the handle 32 is terminated. As illustrated in FIG. 5C, the key is then separated from the guide 24 and removed from the femoral canal. This is accomplished by reversing rotation of the key 28 while exerting a light upward force upon the handle 32. This is done until the surgeon senses that the tabs 34 of the shaft 30, rotated within the annular channel 64 are now aligned with the indentations 52 in the collar 36. When this happens, the key is lifted from the other parts of the tool assembly as illustrated in FIG. 5C.

Removal of the key 28 clears a centered, vertical channel through the guide 24 and the sleeve 26 comprising the circular void center 46 of the collar 36 and the central aperture 48 of the body 38. Such channel permits the insertion of an elongated drill bit 76 into the combination of guide 24 and sleeve 26 as shown in FIG. 5D. The surgeon may now confidently drill through the center of the cement plug 20 (and the optional restrictor 22) without concern about contacting the inner wall 72.

Once a hole has been drilled through the plug 20 (and restrictor 22), the elongated drill bit 76 is removed and the key 28 re-inserted into the collar 36 so that the shaft 30, and attached tabs 34, are rotated within the annular cavity, as illustrated in FIG. 3, to cause reversal of the downward travel of the guide 24 with respect to the sleeve 26. A reduction in the diameter of the expandable sleeve 26 occurs. Once the diameter of the sleeve 26 has been sufficiently reduced from prior contact with the inner wall 72 of the bone, upward pressure on the handle 32 will remove the tool 10 from the canal 70. This permits insertion of an elongated hook through the hole formed by the elongated drill bit 76 followed by upward pressure on the hook to lift the cement plug 20 and the optional restrictor 22 from the canal 70.

Figure 1:
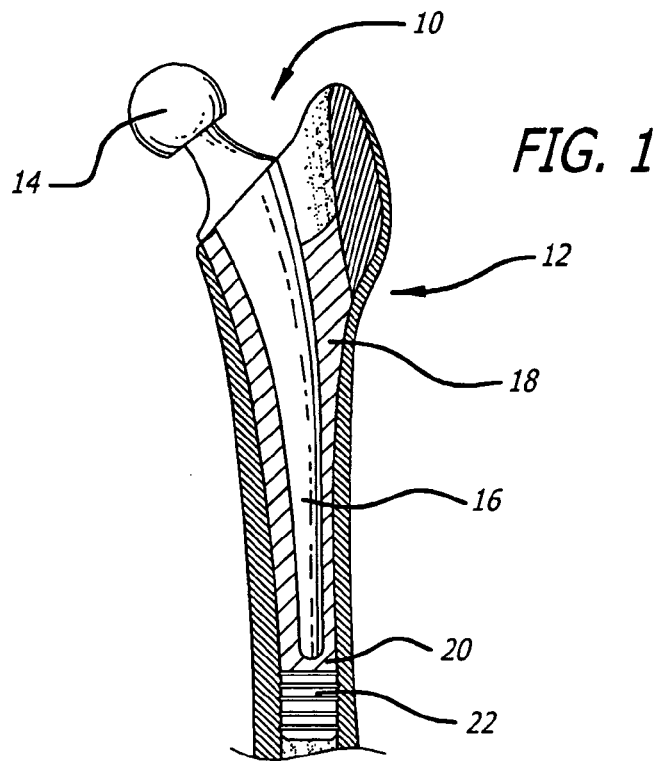
FIG. 1 is a partially sectioned side elevation view for illustrating the portion of a total hip arthroplasty that is addressed by the tool of the present invention.
Figure 6:
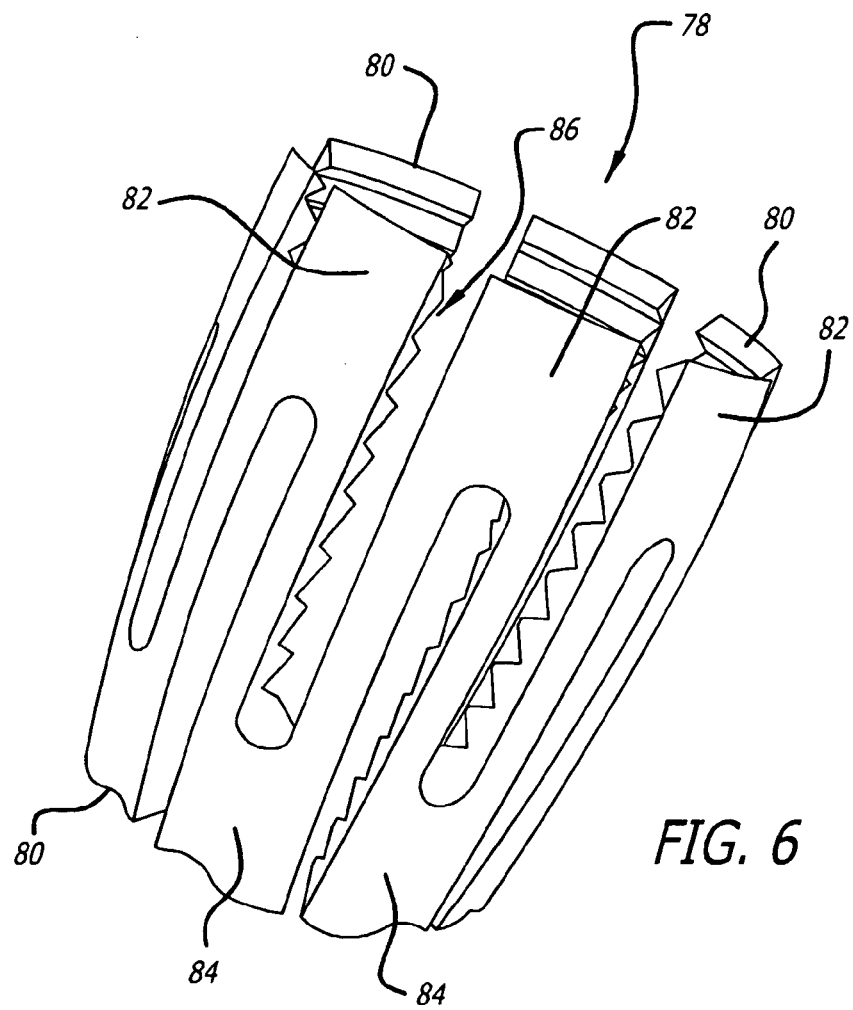
FIG. 6 is a perspective view of a sleeve for a tool in accordance with an alternative embodiment of the invention.

FIG. 6 is a perspective view of a sleeve for a tool in accordance with an alternative embodiment of the invention. Unlike the expandable sleeve 26 comprising three sleeve segments 56 as described above, the expandable sleeve 78 consists of a single piece that has been machined to comprise adjoining longitudinal segments 80 adjoined by alternating top and bottom edge segments 82 and 84 respectively. As in the case of the segmented expandable sleeve 26, the sleeve 78 has an interiorly threaded surface 86 that is tapered for compatibility with the exteriorly-body 38 of the guide 24.

While the sleeve 78 differs from that of the prior figures due, in part, to its integral nature, the presence of a threaded and tapered interior surface 86 coupled with the resilient character of the metal or like material for forming the sleeve 78, assures its operation substantially in accordance with that of the expandable sleeve 26 discussed above.

While the invention has been described with reference to its presently preferred embodiment, it is not limited thereto. Rather, this invention is limited only insofar as it is defined by the following set of patent claims and includes within its scope all equivalents thereof.

What is claimed is:

1. A tool for centering a drill bit within an elongated canal at the interior of bone tissue comprising, in combination:
    a) an exteriorly-threaded guide;
    b) a hollow, interiorly-threaded sleeve comprising (i) a cylinder comprising a plurality of separate elongated cylinder segments and (ii) a band of elastic material surrounding said cylinder;
    c) said sleeve being threadedly engaged to said guide;
    d) the diameter of said sleeve being responsive to rotation of said guide;
    e) a key;
    f) said key comprising an elongated rod having a handle fixed to an end thereof; and
    g) said elongated rod having a plurality of transversely-protruding tabs for engaging said guide so that rotation of said key produces rotation of said guide whereby the diameter of said sleeve is controlled by rotation of said handle.

2. A tool as defined in claim 1 wherein said guide further includes:
    a) an exteriorly-threaded body having opposed top and bottom surfaces separated by a threaded side surface; and
    b) said body being tapered so that the diameter of said top surface exceeds that of said bottom surface.

3. A tool as defined in claim 2 wherein said guide has a longitudinal aperture.

4. A tool as defined in claim 3 further including:
    a) an annular collar; and
    b) said body and said collar are arranged so that a vacant interior of said annular collar surrounds said longitudinal aperture of said body.

5. A tool as defined in claim 4 wherein said aperture is aligned with the longitudinal axis of said truncated cone-shaped guide.

6. A tool as defined in claim 5 wherein said guide further includes means for engaging said key.

7. A tool as defined in claim 6 wherein said means for engaging said key further comprises:
    a) said collar having an annular channel;
    b) said annular channel being continuous with said vacant interior;
    c) at least one screw for securing said collar to said body; and
    d) said at least one screw spanning the height of said annular channel.

8. A tool as defined in claim 7 wherein said annular channel is at the bottom of said collar.

9. A tool as defined in claim 7 including two screws.

10. A tool as defined in claim 1 wherein said key comprises a pin arranged transverse to said rod and exceeding the diameter of said rod in length to comprise a pair of tabs.

11. A tool as defined in claim 1 wherein said cylinder has a serrated bottom edge.

12. A tool as defined in claim 1 wherein an interior of said sleeve is tapered so that the interior diameter of the top of said interior of said sleeve exceeds the interior diameter of the bottom of said sleeve.

13. A tool as defined in claim 1 wherein said band is secured to said cylinder by means of an adhesive.

14. A tool as defined in claim 13 wherein said adhesive comprises a gel that includes cyanoacrylate.

15. A tool as defined in claim 1 wherein said elastic band comprises bicycle tubing.

* * * * *